IMPLANTABLE PENILE PROSTHESIS

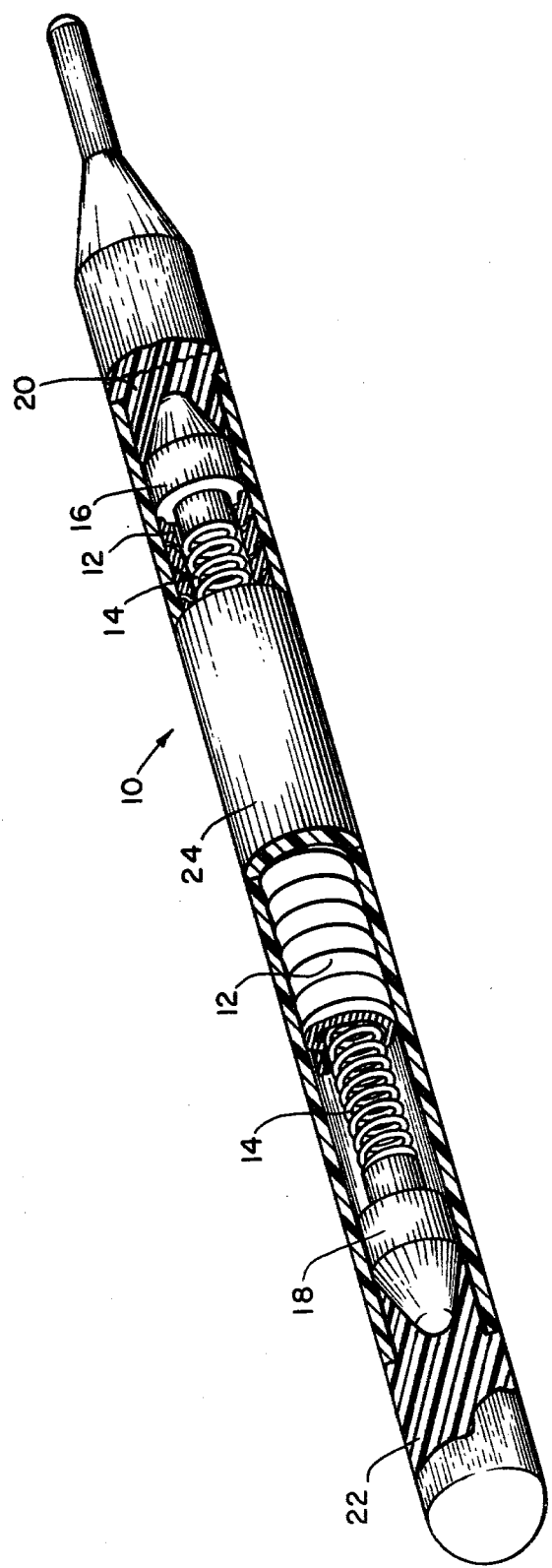

BACKGROUND OF THE INVENTION (1) Field of the Invention

This invention relates to a mechanical penile prosthesis, to its manner of construction, and its use for the treatment of erectile impotence or as a function component of a penile-replacement prosthesis.

(2) Description of The Prior Art

Impotency is not only psychologically based, but can be related to nerve or vascular damage that may have been caused by severe diabetes, multiple sclerosis, spinal-cord injury or surgery in the lower abdomen, such as removal of the bladder or for rectal cancer, or it can also be the result of advanced age, trauma, and the side effects of drugs.

One surgical treatment for impotence involves, in particular, impotence caused by circulatory ills and revascularization (see *Medical World News*, Jan. 10, 1977, pp. 25-27 "Controversy over Penile Implants for Impotence"). While this technique has been proven to be simple and apparently quite successful, it is limited to impotence that is caused by circulatory problems. Accordingly, it cannot be used to help patients with psychogenic or neurogenic impotence.

Another procedure that is being adopted by surgeons for erectile impotence is the use of a penile prosthesis. This treatment is being used not only for impotence caused by age, disease, radical surgery, etc., but is also being used for psychogenic erectile impotence, but only after careful patient evaluation, generally when conventional sex therapy fails.

The modern era of penile implants is but five years old, spawned by development of two new, though very different, prostheses. One emphasizes simplicity, both of surgery and function, but gives the recipient a permanent erection. The other offers the patient a choice of flaccidity or erection, but is costlier, more complex and more prone to mechanical problems.

A simpler prosthesis has been developed (*Medical World News* (supra)) which consists of a rod-like device with a silicone-sponge interior encased in a medical-grade silicone exterior. It is implanted in pairs within the crura and the corpora cavernosa.

A more sophisticated prosthesis comprises a totally implantable device using paired, inflatable, silicone cylinders within the corpora cavernosa connected to a hydraulic pumping device implanted in the patient's scrotum. The fluid reservoir for pumping pressure is placed behind the patient's rectus muscle.

In the impotent patient, the flow of blood to the penis' blood vessels is impaired. The increased flow is necessary for the tissue surrounding the vessels to expand and cause erection. A prosthesis, or artificial device, that causes erection is surgically inserted into the cavities of spongy tissue in the penis. It is these two cavities that normally fill with blood during erection.

With the inflatable device an inert fluid takes the place of the blood supply. Two inflatable silicone tubes are inserted along the side of the penis' spongy tissue. The cylinders are attached by small tubes leading to a fluid-filled sac which is implanted under the patient's lower abdominal muscles. By manipulating the small valves placed under the skin of the scrotum, the patient may fill or empty the penile cylinders with fluid, thus causing erection, also called tumescence, or detumescence.

The big advantage of the inflatable device over the permanently hard silicone rods is aesthetic in that the patient does not have a permanent erection, but insertion of the device requires a more major operation and there are more postoperative complications. The surgical insertion of an inflatable prosthesis, moreover, generally precludes the ability to have a normal unaided erection, although this is not usually true with the non-inflatable device.

SUMMARY OF THE INVENTION

Our invention relates to a simple, mechanical, implantable, penile prosthesis designed to be implanted surgically in the penis for the treatment of erectile impotence or as a functional component of a penile-replacement prosthesis. In particular our invention concerns a mechanical penile prosthesis composed of an elongated, flexible, tubular, gooseneck-type, cylindrical shell or rod element of sufficient stiffness in character and properties to retain its longitudinal position, and yet which resists flexure, but which resistance to flexure may be overriden manually by the user, so that the penile prosthesis may be bent from a flaccid to an erect position by the user by overriding manually the resistance to flexure.

Our penile prosthesis when implanted is longitudinal, incompressible and resists lateral flexure which permits the user and patient to place an otherwise flaccid penis in position to engage in successful copulation. The flaccid posture of the prosthesis allows the patient's penis to rest in a manner that imitates the natural flaccid posture of the penis. The penile prosthesis, which is hermetically sealed within a medically acceptable sheath element, typically is implanted in pairs in a manner such as, for example, set forth in U.S. Pat. No. 4,066,073 issued Jan. 3, 1978, hereby incorporated by reference.

In our preferred embodiment the mechanical penile prosthesis of our invention comprises an elongated, flexible, tubular, gooseneck-type shell or rod-type element, particularly made of metal, such as stainless steel, and composed of annular or helically wound strip material, of the type, for example, employed in "gooseneck lamps" typically where the individual strip elements are linked and crimped or otherwise secured at their edges to adjoining strip elements to provide internal friction and the desired resistance to flexure. The resistance to flexure of the gooseneck-type element is sufficient, so that, when manually implanted, the erect posture is longitudinally incompressible, allowing an otherwise flaccid penis to engage in successful copulation. The flexible gooseneck-type element is stiff and resists flexure, but may be bent manually by the user by simply overriding the element's resistance to flexure. Once the resistance to flexure is overriden by the user or once the flexible hose or gooseneck-type element is bent, it will maintain its longitudinal configuration or straightened as desired by the user. Thus our invention provides for a simple, mechanical, penile prosthesis which upon implantation provides an erect or flaccid penile posture at will. In the flaccid posture of the device the penis is allowed to rest in a manner that imitates the natural faccid posture of the penis, while in the straight or erect posture, it permits the penis to engage in copulation and remains erect without continued manual assistance.

In one embodiment there are end cap means provided at each end of the gooseneck-type element, such as rigid polymeric or plastic end caps, in order to protect the ends of the penile prosthesis from damage. The gooseneck-type element and end caps are encapsulated and sealed within a sheath element, such as of a medically accepted polymeric material, in an elongated fashion, which outer polymeric material seals out body fluids and tissues from the internal structure of the penile prosthesis from the unitary integral prosthesis.

In another embodiment of our penile prosthesis the gooseneck-type shell or rod element may also contain internally therewith the material to impart additional or desired stiffness in flexure to the gooseneck-type element, and preferably comprises a tension-biased element which extends throughout the length of the gooseneck-type element. For example, a stainless-steel, helically coiled, spring element may be used or any other element which imparts additional stiffness and flexure to the prosthesis. Employment of a coiled spring element is desired to increase flexure resistance. Since the coiled spring or tension-biased element would resist bending from a straight position, it tends to help in placing the prosthesis in an erect position and thus provides for an innate flexure resistance to the gooseneck-type element to return to its original position. In the gooseneck-type element the frictional component of the bands of spirally wound metal strip material, which makes up the gooseneck-type element, provides for a frictional component therein, so that the use of the internal helical coil within the gooseneck-type element is desirable to make it easier for the user to assume various penile positions.

Our invention will be described and illustrated in connection with our most preferred embodiment. However, it is recognized and part of our invention that various changes and modifications may be made to the embodiment shown and described by those persons skilled in the art without departing from the spirit and scope of our invention.

BRIEF DESCRIPTION OF THE DRAWING

The drawing illustrates a partially cutaway perspective sectional view of our elongated mechanical penile prosthesis.

DETAILED DESCRIPTION OF THE EMBODIMENT OF THE INVENTION

Figure 1:
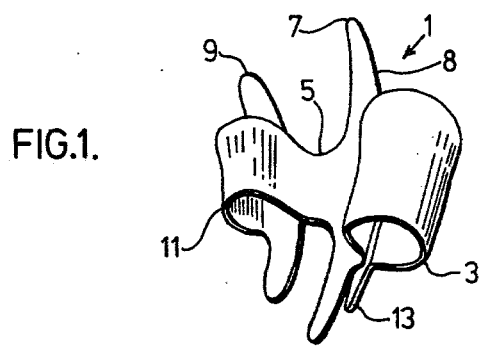
Figure 2:
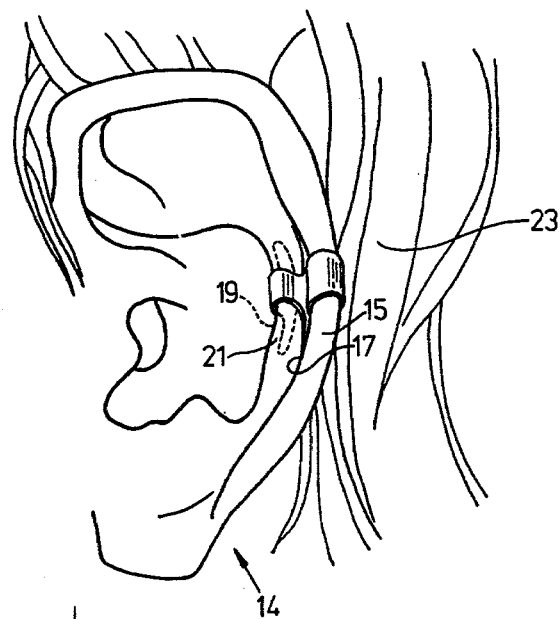
Figure 3:
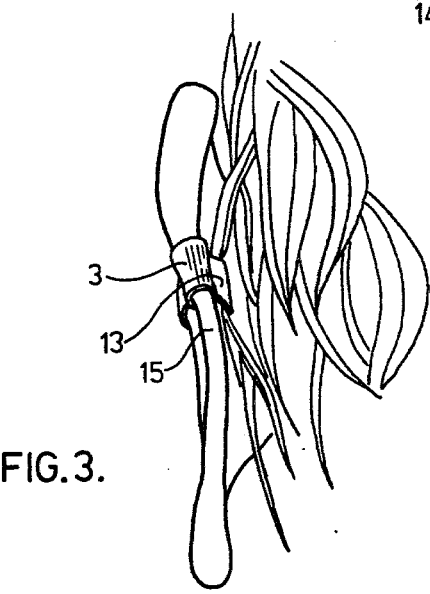

The drawing illustrates our penile prosthesis 10 comprising an elongated flexible tubular gooseneck-type rod or shell element 12, for example, composed of a plurality of helically wound metals, such as stainless-steel strip material, which impart internal friction thereto and resistance to flexure, and which gooseneck-type element contains therein an inner stainless-steel, helically coiled spring 14 which imparts additional and desirable stiffness and flexure to aid in returning the gooseneck tube 12 to a desired position. The gooseneck tube 12 with the coiled spring 14 is stiff and resists flexure, but may be bent manually by the user by simply overriding the resistance to flexure of the combined strip band and composing the tube 12 and coiled spring 14. Once bent by the user the prosthesis will maintain its configuration until it is again bent by the user or placed in the straight and erectile position. At the end of the gooseneck tube 12 are rigid plastic end caps 16 and 18 which fit over the ends of the metal gooseneck tube and which protect the semirigid rubber ends 20 and 22 of the penile prosthesis from damage by the ends of the gooseneck tube 12. The end caps 16 and 18 are so formed to fit the ends of the gooseneck tube 12 and to fit snugly into or be bonded to the rubber ends 20 and 22. The gooseneck tube 12 is sheathed with an outer sheathing element to form a unitary, integral, mechanical, penile prosthesis. The sheathing material is composed typically of a medically accepted polymeric material, such as a flexible silicone rubber tube, which is formed integrally with the silicone rubber ends 20 and 22 of the prosthesis to provide a covering which seals out tissues and body fluids from the internal portion of the prosthesis and permits the prosthesis to be implanted in the penis.

The components of our penile prosthesis may be formed of different and varying materials. However, and typically, the gooseneck-like tube and the helically coiled spring for flexure are formed of a stainless-steel metal, while the end caps are formed from a plastic material and the rubber ends and outer sheathing material of inert polymeric material.

What we claim is:

1. A penile prosthesis adapted for surgical implantation in the penis for the treatment of erectile impotence, which penile prosthesis comprises:
   (a) an elongated, tubular, gooseneck-type, shell element comprising a strip-wound material wherein the edges of adjacent strips are in a contacting relationship to provide internal friction to form the shell element sufficiently stiff in character to retain its position and which resists flexure, but which shell element may be overridden manually to overcome the resistance to flexure by lateral movement thereof;
   (b) means at each end of the gooseneck-type shell element to protect such element; and
   (c) an outer sheathing means surrounding the gooseneck-type shell element and integral with the end means to form a unitary integral penile prosthesis, whereby on implantation the penis may be moved from a flaccid penile position to an erect penile position through the user manually overcoming the resistance to flexure of the gooseneck-type element within the prosthesis.

2. The penile prosthesis of claim 1 wherein the outer sheathing comprises a medically acceptable flexible polymeric materal.

3. The penile prosthesis of claim 2 wherein the polymeric material comprises a silicone rubber or a polyurethane polymeric material.

4. The penile prosthesis of claim 1 which includes plastic end caps, which end caps fit over each end of the gooseneck-type shell element and prevent damage to the end means at each end of the shell element.

5. The penile prosthesis of claim 1 which includes a material within the gooseneck-type shell element to impart resistance to flexure to the gooseneck-type shell element, said material resisting the lateral movement and the bending of the gooseneck-type shell element.

6. The penile prosthesis of claim 5 wherein the material comprises an elongated coiled spring within the gooseneck-type shell element.

7. A penile prosthesis adapted for surgical implantation in the penis for the treatment of erectile impotence, which penile prosthesis comprises:
   (a) an elongated, flexible, metal, gooseneck-type, shell element composed of a metal strip-wound material, the gooseneck-type element stiff in character and which resists flexure, but which may be overridden manually by overcoming the resistance to flexure;

(b) a helical-coil spring within the gooseneck-type element, which spring element resists flexure, but which has a resistance to flexure less than that of the gooseneck-type element;

(c) plastic rigid end cap means at each end of the gooseneck-type shell element to protect such element and the ends of such element;

(d) polymeric ends formed over the end cap means; and (e) a flexible, polymeric, outer sheathing, tubular means about the gooseneck-type element and integral with the polymeric ends of the prosthesis to form a unitary mechanical penile prosthesis, whereby on implantation the penis may be moved from a flaccid penile position to an erect penile position through a manual overcoming by the user of the resistance to flexure of the gooseneck-type element and the helical-coil spring element therein.

8. The prosthesis of claim 1, wherein the gooseneck-type shell element further comprises a helically wound strip material wherein adjacent strips are placed in a contacting relationship by crimping.

9. The prosthesis of claim 1 wherein the gooseneck-type shell element further comprises annular strip-wound materials wherein adjacent annular strips are placed in a contacting relationship by crimping.

* * * * *